June 29, 1971 R. L. KENNEDY Re. 27,150

DEVICE FOR PREVENTING HYPOTENSION SYNDROME OF LATE PREGNANCY

Original Filed March 7, 1966

INVENTOR.
ROLAND L. KENNEDY

BY Fraser & Fraser
ATTORNEYS

United States Patent Office

Re. 27,150
Reissued June 29, 1971

27,150

DEVICE FOR PREVENTING HYPOTENSION SYNDROME OF LATE PREGNANCY

Roland L. Kennedy, 4639 Farmington Road, Toledo, Ohio 43623

Original No. 3,389,702, dated June 25, 1968, Ser. No. 532,328, Mar. 7, 1966. Application for reissue Dec. 26, 1968, Ser. No. 799,137
Int. Cl. A61b *17/42*
U.S. Cl. 128—361 5 Claims

Matter enclosed in heavy brackets [ ] appears in the original patent but forms no part of this reissue specification; matter printed in italics indicates the additions made by reissue.

ABSTRACT OF THE DISCLOSURE

A device for maintaining normal blood pressure during late pregnancy comprising a pad for engaging the body of a woman to displace the uterus to the left to prevent the inferior vena cava from compression to permit normal cardiac output. Linkage means are provided to interconnect the body engaging pad with the side rail of an operating table to enable adjustment of the pad relative to the patient.

When women in the latter part of their pregnancy lie supine, obstruction of the inferior vena cava from compression by the uterus may occur. As a result, the venous return to the heart is reduced which in turn lowers the cardiac output. Typically, the heart rate increases, the blood pressure drops, and the patient assumes a shock-like appearance. This has been called hypotensive syndrome of late pregnancy. Simply turning the patient on her side relieves the obstruction and the circulation is restored.

Just prior to delivery when the patient is placed in the lithotomy position, the situation again exists for the production of the supine hypotensive syndrome. Since the patient cannot be turned on her side at this time, the uterus must be displaced to the left side relieving the abdominal venous compression. Such procedure will produce prompt results with the blood pressure returning to satisfactory levels by the time subsequent determinations of blood pressure can be made.

The present invention is concerned with the production of a device which will provide for the maintenance of a normal blood pressure of a patient prior to delivery and prevent fetal anoxia from inadequate circulation of the placenta.

It is an object of the present invention to produce a device for preventing hypotensive syndrome of late pregnancy.

It is a further object of the invention to produce a device for preventing hypotensive syndrome of late pregnancy which is easy to employ and economic to manufacture.

The above objects and advantages of the invention may be readily achieved by a combination with the obstetrical table having a side rail of a surgical device for preventing hypotensive syndrome of late pregnancy comprising bracket means for selective slidable engagement with the side rail of the surgical table; a body engaging pad; and linkage means for connecting said body engaging pads to said bracket means, said linkage means including a first longitudinally adjustable strap means extending horizontally inwardly from said bracket means and a second adjustable strap means connected to said first strap means extending upwardly and inwardly therefrom.

Other objects and advantages of the invention will become readily apparent from reading the following detailed description of a preferred embodiment of the invention when considered in the light of the accompanying drawings, in which.

Figure 2:
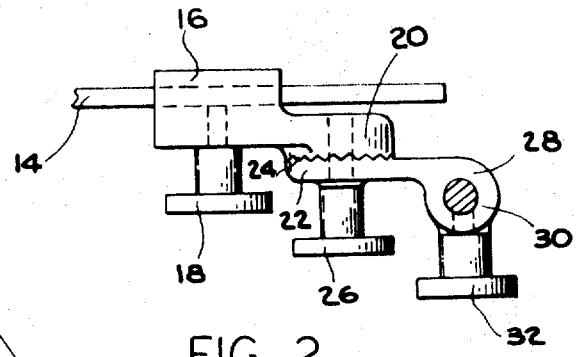
FIGURE 2 is a fragmentary sectional view of the invention taken along line 2—2 of FIGURE 1.
Figure 1:
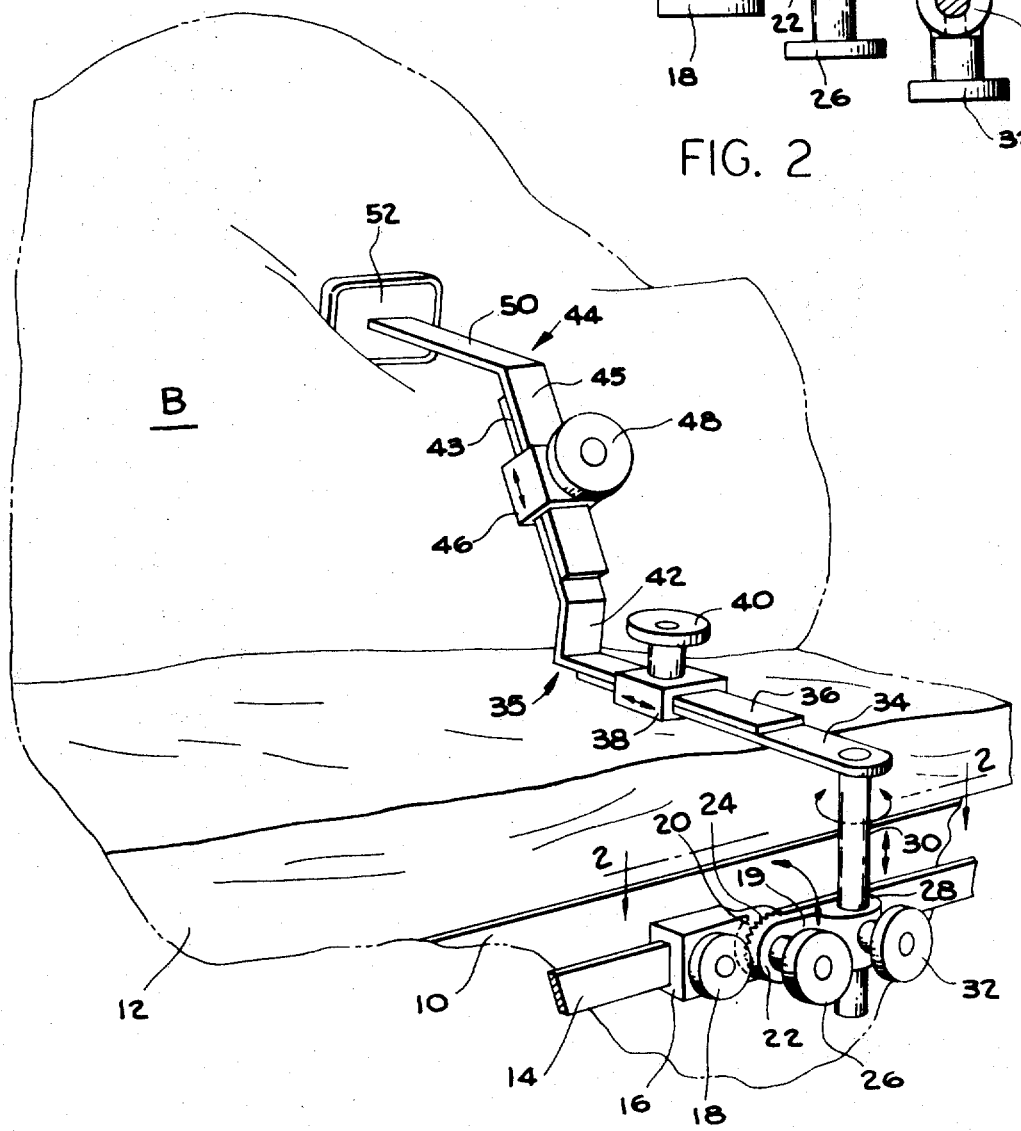
FIGURE 1 is a fragmentary perspective view of the device of the invention.

Referring to FIGURE 1, there is shown an obstetrical table top 10 having a padding 12 thereon for supporting a body of a patient, generally indicated by reference B. Adjacent the side of the table 10 is a horizontal longitudinally extending side rail 14 which is typically employed to support numerous and varied surgical appliances.

The device of the invention is adapted to be supported for selective positioning on the side rail 14 by a sliding bracket 16 having a conventional set screw 18, which upon being loosened, will allow the bracket 16 to freely slide on the side rail 14 and upon being tightened will selectively fix the position of the bracket 16 on the side rail 14.

A member 19 is adjustably affixed to the bracket 16 by means of a pair of disc-like elements 20 and 22 having cooperating crown teeth 24. It will be appreciated that the element 20 is integral with the bracket 16, while the element 22 is integral with the member 19. Angular adjustment of the member 19 with respect to the bracket 16 is effected by loosening an associated set screw 26; effecting the desired adjustment; and then tightening the set screw 26.

The member 19 is provided with an elongate aperture 28 for receiving a portion of a shank 30. A set screw 32 is associated with the member 19 and is effective for the selective adjustment of the shank 30 within the aperture 28. It will be appreciated that upon loosening the set screw 32, the shank may be adjusted both up and down within the aperture 28 and also will enable that the shank element to be angularly or rotatingly positioned therewithin.

The upper end of the shank 30 is provided with a strap 34 which is adapted to extend in a horizontal direction away from the shank 30, and typically is positioned to overlie the upper surface of the padding 12. Another strap 35 having a relatively horizontally disposed section 36 is positioned above the upper surface of the strap 34 and is adapted to slide thereon. A bracket 38 surrounds the strap 34 and section 36 of the strap 35 and includes a set screw 40 which will, upon tightening, fix the position of the straps relative to one another.

The innermost portion of the strap 36 is formed to extend upwardly as indicated by reference numeral 42 and then inwardly as indicated by a reference numeral 43. Cooperating with the uppermost portion 43 of the strap 35, there is another strap 44 having a portion 45 positioned above the outer surface of the portion 43 of the strap 35 and is adapted to slide thereon. A bracket 46 surrounds the portions 43 and 44 of the straps 35 and 44, respectively, and includes a set screw 48, which will, upon tightening, fix the position of the straps relative to one another. The uppermost portion 50 of the strap 44 is formed to extend inwardly of the portion 45 and the free end thereof is adapted to carry a body engaging pad 52. It will be noted that the pad 52 is in a substantially vertical position and in operation is positioned against the patient to displace the uterus to relieve the abdominal venous compression which would normally occur in women in the latter part of their pregnancy. It will be readily apparent that cooperative adjustment of the strap elements 35 and 44 will be effective to dispose the pad 52 in the desired position against the patient B.

When the device above described is not being used, the set screw 32 is loosened and the entire assembly may be turned to rotate the shank 30 about its axis with the aper- ıre 28 to a point where the strap elements 34, 35, and 44 :side along the side of the table 10. Then, the set screw 2 is tightened, and the set screw 26 is loosened allowing ıe entire assembly to drop to an inoperative position be- ›w the table 10.

While the illustrated embodiment of the invention ıows the linkage means between the bracket 16 and the ıd 52 as being in the form of relatively flat elongated raps, the adjustment of the pad could likewise be chieved by telescoping rod-like members of a similar onfiguration.

In accordance with the provisions of the patent statutes have explained the principle of mode of operation of ıy invention and have illustrated and described what I ow consider to represent its best embodiment. However, desire to have it understood that within the scope of the ppended claims, the invention may be practiced other- ·ise than as specifically illustrated and described.

What I claim is:

1. In a combination with an obstetrical table having a de rail, a device for preventing hypotensive syndrome f late pregnancy comprising:

bracket means for selective slidable engagement with the side rail of the obstetrical table;

a body engaging pad for engaging the body of a woman to displace the uterus to the left to prevent the inferior vena cava from compression to permit normal cardiac output; and linkage means connecting said body engaging pad to said bracket means, said linkage means including a first longitudinally adjustable strap means extending horizontally inwardly from said bracket means and a second adjustable strap means selectively slidably connected to said first strap means and extending upwardly and inwardly therefrom whereby cooperative adjustment of said first and second strap means will selectively position said body engaging pad over the obstetrical table whereby when said body engaging pad is positioned against a patient on the table obstruction of the interior vena cava is prevented from compression by the uterus to avoid hypotension.

2. The invention defined in claim 1 the first adjustable rap means of said linkage means includes a depending shank, and said bracket means includes an apertured portion for receiving said shank.

3. The invention defined in claim 2 wherein said bracket means includes means for selectively securing the shank of said linkage means within the apertured portion of said bracket means.

4. The invention defined in claim 1 wherein said linkage means includes threaded means providing adjustment between said first and second trap means.

*5. In combination with an obstetrical table having a side rail, a device for preventing hypotensive syndrome of late pregnancy comprising:*

*bracket means for selective slidable engagement with the side rail of the obstetrical table;*

*a body engaging pad for engaging the body of a woman to displace the uterus to the left to prevent the inferior vena cava from compression to permit normal cardiac output; and*

*linkage means connecting said body engaging pad to said bracket means, said linkage means including a first strap means extending from said bracket means and second adjustable strap means selectively slidable connected to said first strap means and extending upwardly and inwardly therefrom whereby cooperative adjustment of said first and second strap means will selectively position said body engaging pad over the obstetrical table whereby when said body engaging pad is positioned against a patient on the table obstruction of the inferior vena cava is prevented from compression by the uterus to avoid hypotension.*

References Cited

The following references, cited by the Examiner, are of record in the patented file of this patent or the original patent.

UNITED STATES PATENTS

| | | | |
|---|---|---|---|
| 1,625,682 | 4/1927 | Ragg | 269—328 |
| 1,894,991 | 1/1933 | Hayes | 248—279X |
| 2,608,192 | 8/1952 | Heitmeyer et al. | 128—20 |
| 2,642,250 | 6/1953 | Kasnowich | 5—317X |
| 3,221,743 | 12/1965 | Thompson et al. | 128—303 |

DALTON L. TRULUCK, Primary Examiner